United States Patent
Fox et al.

(10) Patent No.: US 6,214,611 B1
(45) Date of Patent: Apr. 10, 2001

(54) PROCESS FOR THE PREPARATION OF PROSTAGLANDIN PRECURSORS

(75) Inventors: Martin Edward Fox, Cambridge; Julian Simon Parratt, Anglesey, both of (GB)

(73) Assignee: Chirotech Technology Limited (GB)

(*) Notice: Subject to any disclaimer, the term of this patent is extended or adjusted under 35 U.S.C. 154(b) by 0 days.

(21) Appl. No.: 09/548,076

(22) Filed: Apr. 12, 2000

Related U.S. Application Data

(60) Provisional application No. 60/136,181, filed on May 27, 1999.

(30) Foreign Application Priority Data

Apr. 12, 1999 (GB) .................................................. 9908327

(51) Int. Cl.[7] .................................. C12P 7/22; C12P 7/62; C12N 9/16; C12N 9/18

(52) U.S. Cl. .......................... 435/280; 435/135; 435/196; 435/197; 435/156

(58) Field of Search ..................................... 435/156, 280, 435/135, 197, 196

(56) References Cited

U.S. PATENT DOCUMENTS 4,321,275  3/1982  Bowler et al. .

FOREIGN PATENT DOCUMENTS 209290    11/1981  (CS) .
0639563   3/1994   (EP) .
9533845   12/1995  (WO) .
9723223   7/1997   (WO) .

OTHER PUBLICATIONS

Tolstikov, G. et al. (1983) "Prostanoids. 16–aryloxy [17.18.19.20] tetranor prostaglandins" *Zh. Org. Khim.*19(9):1857–1866. (abstract).

*Primary Examiner*—Herbert J. Lilling
(74) *Attorney, Agent, or Firm*—Saliwanchik, Lloyd & Saliwanchik

(57) ABSTRACT

A propargylic alcohol, enriched in the (R)-enantiomer, has the formula

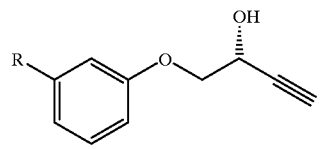

wherein R is $C_{1-4}$ alkoxy, halogen, or $C_{1-4}$ alkyl optionally substituted by OH or halogen. This is prepared by the steps of:

(a) enantioselective (R)-esterification of the racemic alcohol using any acyl donor and a first enzyme;
(b) removal of the untreated (S)-alcohol; and
(c) enantioselective hydrolysis of the (R)-ester, using a second enzyme.

13 Claims, No Drawings

PROCESS FOR THE PREPARATION OF PROSTAGLANDIN PRECURSORS

CROSS-REFERENCE TO A RELATED APPLICATION

This application claims the benefit of U.S. Provisional Application No. 60/136,181, filed May 27, 1999.

FIELD OF THE INVENTION

This invention relates to the preparation of prostaglandin omega side chains in optically enriched form.

BACKGROUND OF THE INVENTION

Synthetic prostaglandins with a 4-aryloxy-3-hydroxy-1-(E)-butenyl omega chain, in particular 16-[3-(trifluoromethyl)phenoxy]-17, 18, 19, 20-tetranor-PGF$_{2a}$ and its esters, more particularly the isopropyl ester, are potent drugs for the treatment of glaucoma and ocular hypertension. The use of 11-oxaprostaglandins with 4-aryloxy-3-hydroxyl-1-(E)-butenyl side chains for this purpose is disclosed in WO-A-97/23223. The desired activity resides in the dextrorotary 15 R isomeric form. The structure of (+)-16-[3-(trifluoromethyl)phenoxy]-17, 18, 19, 20-tetranor-PGF$_{2a}$, isopropyl ester, is shown below.

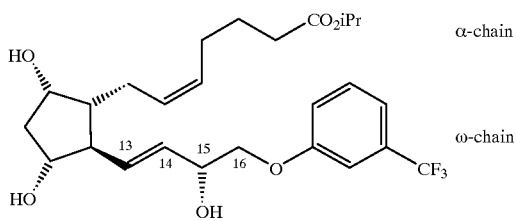

U.S. Pat. No. 4,321,275 discloses a synthesis of the corresponding racemic free acid fluoprostenol, for use as a luteolytic agent and stimulant of uterine smooth muscle contraction in vertinary medicine. This compound is prepared from the Corey lactone aldehyde 4β-formyl-2,3,3aβ, 6aβ-tetrahydro-2-oxo-5α-(4-phenylbenzoyloxy)-cyclopenteno[b]furan, by reaction with dimethyl 2-oxo-3-[3-(trifluoromethyl)phenoxy]-oxypropylphosphonate, thus introducing C14–16 of the omega chain. The resulting enone is transformed to fluoprostenol by non-stereoselective reduction of the keto function to the corresponding alcohol, removal of the 4-phenylbenzoyl group, protection of the two hydroxy groups with tetrahydropyranyl, reduction to the lactol, Wittig olefination with the ylide prepared from (4-carboxybutyl)triphenylphosphonium bromide and removal of the tetrahydropyranyl groups. The active 15 R diastereoisomer is obtained by chromatographic separation.

EP-A-0639563 discloses the preparation of enantiomerically enriched 16-[3-(trifluoromethyl)phenoxy]-17,18,19, 20-tetrano-PGF$_{2\infty}$isopropyl ester. The active 15 R diastereoisomer of the analogue, 16-(3-chlorophenoxy)-17,18,19, 20-tetranor-PGF$_{2\infty}$isopropyl ester was formed stereoselectively by reduction of the keto function of the corresponding Corey lactone enone with (−)-B-chlorodiisopinocampheylborane.

The omega chain of prostaglandins may also be introduced in its entirety by means of a coupling reaction between an organocuprate reagent and an electrophilic cyclopentane core synthon. This has the advantage of being a more convergent strategy, whereby the omega chain can be introduced already containing the requisite chirality.

Danilova et al, *DOKL Chem. USSR (Engl. Transl.)*, 1983 273, 375–377, disclose an organocuprate coupling reaction of an alkenylcuprate formed from racemic 4-(3-trifuloromethylphenoxy)-3-(1-ethoxyethoxy)-1-iodo-1E-butene and a 2-cyclopentenone, to prepare an 11-deoxy analogue of fluoprostenol.

Tolstikov et al, *J. Org. Chem. USSR (Engl. Transl)*, 1983, 19, 1624–1631 also disclose the racemic precursors to this 1-ethoxyethoxy ether, which are 4-[(3-trifluoromethyl)phenoxy]-1-butyn-3-ol, 4-(3-trifluoromethylphenoxy)-1-iodo-1E-buten-3-ol and their corresponding trimethylsilyl ethers.

The use of an enantiomerically enriched omega chain precursor for the preparation of PGF$_{2a}$, in which the key step is the coupling of an alkenylcuprate reagent to a tricycloheptanone, is disclosed by Davies et al, *J. Chem. Soc., Perkin Trans* 1, 1981, 1317).

WO-A-95/33845 discloses the preparation of an enantiomerically enriched propargyl alcohol of the formula

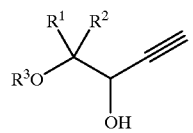

wherein R$^1$ and R$^2$ are each H or alkyl, and R$^3$ is optionally substituted phenyl, alkyl or cycloalkyl, by enantioselective enzyme-mediated bioresolution of the corresponding racemate. In the Examples, racemic 3-hydroxy-4-phenoxy-1-butyne was treated with isopropenyl acetate and lipase PS; the (S)-alcohol was obtained in 98% ee. The (R)-alcohol was obtained in 96% ee by non-enzymatic hydrolysis of the (R)-ester formed in the bioresolution step.

SUMMARY OF THE INVENTION

This invention is based on the discovery that, in order to obtain the single enantiomer of a 4-aryloxy-3-hydroxy-1-(E)-butene, for the ultimate provision of a prostaglandin omega side chain, the procedure of WO-A-95/33845 is not invariably satisfactory. In particular, relatively low ee's are obtained when the aryl group is meta-substituted, e.g. with a key CF$_3$ of Cl group. An effective synthesis of prostaglandin agents with these omega side chains, in particular for 16-(3-trifluoromethylphenoxy)-17,18,19,20-tetranor PGF$_{2a}$ and its ester derivatives has been found.

According to the present invention, a process for the preparation of a propargylic alcohol, enriched in the (R)-enantiomer, of the formula

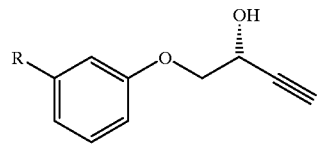

wherein R is C$_{1-4}$ alkoxy, halogen, or C$_{1-4}$ alkyl optionally substituted by OH or halogen, comprises the steps of:
(a) enantioselective (R)-esterification of the racemic alcohol using an acyl donor and a first enzyme,
(b) removal of the unreacted (S)-alcohol; and
(c) enantioselective hydrolysis of the (R)-ester, using a second enzyme.

The propargylic alcohol may then be converted to a protected allylic alcohol of the formula

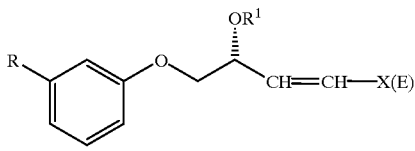

wherein R is as defined above, R¹ is a blocking group, and X is a metal or a metal-containing group such that the compound is an organometallic reagent or X is a group convertible thereto, which comprises the above steps and, additionally, (d) introducing the blocking group;
(e) converting the C≡C group to the (E)—CH═CH—X group.

The allylic alcohol may then be converted to a prostaglandin having a ω-side chain including the group

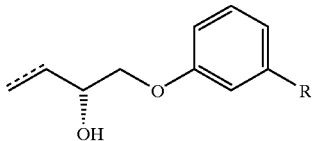

wherein R is a defined above, which comprises the above steps; if X is the convertible group, converting it to a metal or metal-containing group; and converting the organometallic allylic alcohol to the prostaglandin. This conversion can be done by known means; see references cited above. This conversion is facilitated by the discovery that 8-anti{4-[3-(trifluoromethyl)phenoxy]-3-R-dimethyl-tert-butylsilyloxy-1E-butenyl}-6-endo-dimethyl-tert-butylsilyloxy-2-oxabicyclo[3.2.1]octan-3-one can be isolated in crystalline form, as described and claimed in the copending Patent Application, filed on the same date, entitled "Novel Intermediate for the Synthesis of Prostaglandins", and claiming priority from British Patent Application No. 9908326.3.

The process of the invention can provide novel prostaglandin ω-side chain precursors having good ee values, in excess of 80%, preferably at least 97% and most preferably at least 99%. In particular, the present invention provides the (R)-propargylic alcohol in at least 97%, preferably at least 99% ee.

DESCRIPTION OF THE INVENTION

As indicated above, the process of the invention gives a propargylic alcohol that can be readily converted to a trans-alkenylcuprate reagent used to join the omega chain to a synthon for the cyclopentane or other prostaglandin core component. This alkenylcuprate reagent may be prepared from a corresponding simple trans-alkenylmetal derivative, e.g. the trans-alkenyllithium, in which the hydroxy group is protected with a base stable group, e.g. tert-butyldimethylsilyl. The preparation of this trans-alkenylmetal derivative may be either by metallation of the corresponding halide (X=halide, preferably iodide), e.g. by formation of the alkenyllithium with tert-butyllithium, or by hydrometallation of the corresponding alkyne, e.g. with the reagent formed from zirconocene dichloride and tert-butylmagnesium chloride. The trans-alkenyl iodide may be prepared by reaction of a trans-alkenylmetal derivative which may formed by hydrometallation of the alkyne, e.g. the trans-alkenylzirconocene chloride with an electrophilic iodine source, e.g. iodine. The alkyne may be prepared from the corresponding propargylic alcohol by reaction with a protecting group donor, e.g. tert-butyldimethychlorosilane.

A key aspect of the present invention relates to the preparation of the enantionmerically enriched (R)-propargylic alcohol, from the corresponding racemic propargylic alcohol. This involves two enzymatic reactions, using the same or (more usually) different enzymes. Step (c) involves cleavage of a carboxylate ester with enhancement of enantiomeric excess, e.g. hydrolysis of the butyrate ester with an enzyme. In one example of step (b), the carboxylate ester is prepared by inversion of the sulfonate ester in a mixture of the (R)-carboxylate ester and (S)-sulfonate ester, using a carboxylic acid or carboxylate salt, e.g. by reaction of the mesylate with triethylammonium butyrate. The mixture of (R)-carboxylate ester and (S)-sulfonate ester may be prepared by sulfonylation of a mixture of (R)-carboxylate ester and (S)-propargylic alcohol obtainable by enantioselective esterification of the racemic alcohol (step(a)), e.g. with vinyl butyrate or vinyl propionate and an enzyme. Alternatively, in step (b), the (R)-carboxylate ester may be isolated directly from the mixture of (R)-carboxylate ester and (S)-alcohol obtained by step (a), by treatment with a source of sulfur trioxide, e.g. sulfur trioxide-pyridine complex, to form the (S)-hemisulfate ester which may be preferentially extracted into aqueous base.

An illustrative preparation of the required omega chain iodide in enantiomerically enriched form, from the racemic propargylic alcohol, wherein R¹ is tert-butyldimethylsilyl and R³ represents the meta-substituted phenyl group, will now be described in greater detail, with reference to Scheme I.

Step (i) of the Scheme is the enantioselective esterification reaction (step (a) above). This is achieved using an appropriate acyl donor and an enzyme, preferably vinyl butyrate or vinyl propionate and Mucor miehei lipase. This reaction may be conducted in a non-polar solvent, preferably heptane. Mucor miehei lipase is preferred for this step, following a screening of available enzymes conducted using the propargylic alcohol in which R is $CF_3$. In this preliminary screen, also using Novozyme, Lipase AK, Chirazyme L2 (immobilised Candida antartica lipase, from Boehringer Mannheim) and Lipase PS (Pseudomonas cepecia lipase, from Amano), Lipozyme (immobilised Mucor miehei lipase, from Novo) gave the best results in terms of enantioselectivity.

Step (ii) is the sulfonylation reaction. This is achieved using a base, which may be triethylamine and an appropriate sulfonyl donor, preferably methanesulfonyl chloride.

Step (iii) is the inversion reaction. This is achieved with a carboxylic acid or carboxylate salt, preferably butyric or propionic acid or a butyrate or propionate salt which may be triethylammonium butyrate or propionate.

Step (iv) is a purification procedure for removal of residual propargylic alcohol from the carboxylate ester, following either step (i) or (iii). This is achieved by formation of the corresponding acid half ester, preferably the hydrogen sulfate, using a diacid anhydride which may be a complex of sulfur trioxide, preferably sulfur trioxide-pyridine complex or an acid chloride and base, preferably chlorosulfonic acid and pyridine, and then partitioning with a basic aqueous medium, preferably sodium bicarbonate solution.

Step (v) is the cleavage of the carboxylate ester with enhancement of the enantiomeric excess (step (c) above). This may be achieved by basic hydrolysis using an appropriate enzyme, e.g. Mucor miehei lipase, but Candida antarctica lipase is preferred. As for step (i), suitable anzymatic activity can readily be determined by the skilled person, based on existing knowledge and the information presented herein. The appropriate reaction conditions, e.g. solvent can also be readily determined.

Step (vi) is the coupling of the (R)-propargylc alcohol with a base-stable protecting group, preferably a silyl group, most preferably tert-butyldimethylsilyl. This may be achieved with an appropriate protecting group donor and a base, preferably a silyl chloride, most preferably tert-butyldimethylsilylchlorosilane and imidazole.

Step (vii) comprises an optional purification procedure for removal of any residual carboxylate ester present as an impurity in the silyl ether. This is achieved by cleavage of the ester using a base in an alcoholic medium, preferably potassium carbonate in methanol, and then formation of the corresponding acid half ester, which may be the hemiphthalate or hydrogen sulfate, by reaction with a diacid anhydride, which may be phthalic anhydride or sulfur trioxide pyridine complex, or an acid chloride and base, preferably chlorosulfonic acid and pyridine, and then partitioning with a basic aqueous medium, preferably sodium carbonate solution.

Step (viii) is the hydrometallation-halogenation reaction of the protected (R)-propargylic alcohol. This is achieved by reaction with a metal hydride, preferably the reagent formed from zirconocene dichloride and tert-butylmagnesium chloride, and then a halogenating reagent, preferably iodine. The terminal alkene, where H is present in place of X, is a by-product of this step and does not affect the use of the trans-alkenyl halide as an omega side-chain component in the preparation of 4-aryloxy-3-hydroxy-1-(E)-butenyl prostaglandins.

The inversion procedure may be omitted from the process. Thus, if steps (ii) and (iii) are omitted, after step (iv), (R)-ester is also obtained which may be used directly in step (v). If this abbreviated process is used, then the (R)-ester is typically of higher enantiomeric excess (>90%) than obtained after the inversion procedure, hence the (R)-alcohol obtained after step (v) contains less (S)-ester. Steps (vii) and (viii) may also be omitted, a simple purification procedure, e.g. filtration through a silica gel column with a non-polar eluant, e.g. heptane, being sufficient for removal of the remaining (S)-ester. This abbreviated process has the disadvantage that the overall yield can never exceed 50%, but the advantage that four fewer chemical steps are required. Steps (vii) and (viii) may also be omitted if purification of the (R)-alcohol after step (v) by recrystallisation is possible even when the inversion procedure is used.

Thus, the present invention provides a practical route by means of certain novel intermediates, to the novel synthon for 4-aryloxy-3-hydroxy-1-(E)-butenyl prostaglandin omega side-chains, in particular the 16-(3-aryloxy)-17,18,19,20-tetranor-PGF$_{2a}$ omega chain. The cleavage of the carboxylate ester using a second enzymatic reaction allows the (R)-propargylic alcohol to be obtained in greater enantiomeric excess than may be achieved using a single enzymatic reaction.

The following Examples illustrate the invention.

EXAMPLE 1
Bioresolution of 4-[3-(trifluoromethyl)phenoxy]-1-butyn-3-ol

The racemic propargylic alcohol (852 g, 3.70 mol) is charged to a 10 L jacketed vessel. Heptane (4300 ml) and vinyl butyrate (580 ml, 4.82 mol) are added and the mixture is equilibrated to 22° C., with efficient stirring under an atmosphere of nitrogen. Mucor miehei lipase (173 g) is added to the mixture which is then stirred for 43 hours at 22° C. The suspension is filtered, the residues are washed with heptane (1200 ml) and the filtrates are combined before evaporating the solvent under reduced pressure. The residue is dissolved in toluene (1500 ml) and the solution is washed with saturated aqueous sodium bicarbonate solution (2×550 ml). The combined aqueous washings are extracted with toluene (1×300 ml) and the combined toluene solutions are washed with saturated aqueous sodium chloride solution (1×500 ml), dried over anhydrous magnesium sulfate, filtered and the solvent is removed under reduced pressure to afford an equimolar mixture (1059 g) of the (S)-alcohol to (92.8% ee) and the corresponding (R)-butyrate ester (96.7% ee). Data extrapolated from these two ee values obtained by chiral GC analysis, indicates that the reaction was terminated at 49.1% conversion and has an entantiomeric ratio (E) of 222.

EXAMPLE 2
Mesylation

The (1:1) alcohol/butyrate ester mixture (1059 g, 2.00 mol in alcohol) is dissolved in dichloromethane (4000 ml), the solution is equilibrated to 0° C., and triethylamine (640 ml, 4.60 mol) is added. The solution is allowed to return to 0° C. and a solution of methanesulfonyl chloride (200 ml, 2.34 mol) in dichloromethane (400 ml) is added dropwise over 2 hours, maintaining a reaction temperature of <2° C. Upon complete addition, the reaction is stirred for 1 h at <2° C., and extra triethylamine (60 ml, 0.45 mmol) and methanesulfonyl chloride (20 ml, 0.29 mmol) in dichloromethane (60 ml) are added. The solution is stirred for a further 1 h at <2° C. before water (1500 ml) is added with rapid stirring over 10 minutes at <5° C. After allowing the phases to partition, the two layers are separated. The organic phase is washed with 1.5 N hydrochloric acid (1500 ml) and saturated aqueous sodium bicarbonate solution (800 ml). The organic solution is dried over anhydrous magnesium sulfate and filtered, and the solvent is removed under reduced pressure to yield a clear, pale brown oil (1123 g). GC analysis indicated that the mesylate/butyrate mixture contains no residual alcohol.

EXAMPLE 3
(R)-4-[3-(Trifluoromethyl)phenoxy]-1-butyn-3-yl butyrate

Triethylamine (327 ml, 2.35 mol) is added to a butyric acid (230 ml, 2.52 mol) over 40 minutes in a nitrogen-purged flask, maintaining the temperatures below 10° C. The butyrate ester/mesylate (1:1) mixture (1123 g, 1.85 mol in methanesulfonate) is added and the solution is heated to 110–120° C. for 3–4 hours. After allowing the solution to cool to room temperature, heptane (1600 ml), saturated sodium bicarbonate solution (800 ml) and water (800 ml) are added. The mixture is stirred vigorously, and the phases are allowed to partition. The aqueous layer is extracted with heptane (300 ml), and the combined organic extracts are washed with 1.2 N hydrochloric acid (800 ml) and saturated sodium bicarbonate solution (800 ml). The organic layer is dried over anhydrous magnesium sulfate, filtered and the solvent is removed under reduced pressure to yield the crude (R)-butyrate as a brown liquid (907 g). Chiral GC analysis indicated the enantiometric excess was shown to be 92.6%, and achiral GC showed some propargylic alcohol to be present.

EXAMPLE 4
Removal of residual propargylic alcohol from crude (R)-4-[3-(trifluoromethyl)phenoxy]-1-butyn-3-yl butyrate DMF (1 L) is added to the crude (R)-butyrate (907 g, 3.02 mol) under a nitrogen. Sulfur trioxide-pyridine complex (45 g, 0.28 mol) is added in over 5 minutes. The solution is stirred for 1–2 hours, then diluted with heptane (1.8 L). Saturated sodium bicarbonate solution (2.3 L) is added over 15 minutes. The layers are separated, and the aqueous phase is extracted with heptane (0.5 L). The combined organic phases are washed with 10% potassium hydrogen sulfate solution (0.9 L) and saturated sodium bicarbonate solution (0.9 L). The organic layer is dried over anhydrous magnesium sulfate, filtered and concentrated under reduced pressure, to provide the crude (R)-butyrate free of alcohol by GC as a yellow to brown oil (865).

EXAMPLE 5

(R)-4-[3-(Trifluoromethyl)phenoxy]-1-butyn-3-ol where the butyrate excess is <90%

Potassium dihydrogen phosphate (30.6 g, 0.225 mol) is placed in a 10 L jacketed vessel, fitted with a thermometer and pH probe. Water (4.4 L) is added, and the suspension is stirred until the solid has dissolved. The solution is titrated to pH 7.0 with 2 N potassium hydroxide solution and equilibrated to 30° C. A solution of the butyrate ester (865 g, 288 g) in heptane (850 ml) is added. Candida antarctica lipase (16.8 g) is added and the reaction is stirred at 30° C. while titrating to pH 7 using 4 N sodium hydroxide solution. After 3 hours toluene (0.7 L) is added and the enzyme is removed by filtration. The organic phase is separated and the aqueous phase is extracted with toluene (400 ml). The combined organic solutions are washed with saturated aqueous sodium bicarbonate solution (2×700 ml), dried over anhydrous magnesium sulfate, filtered and the solvent evaporated under reduced pressure to yield the crude (R)-alcohol (740 g, 99% ee by chiral GC) containing unwanted (S)-butyrate ester (57% ee by chiral GC).

EXAMPLE 6

(R)-4-[3-(trifluoromethyl)phenoxy]-3-(tert-butyldimethylsilyloxy)-1-butyne

The crude (R)-alcohol (740 g about 75% pure, 2.41 mmol) is dissolved in DMF (1 L) and the solution is placed in a nitrogen-purged flask. Imidazole (214 g, 3.14 mol) is added. The solution is cooled to 0° C. and tert-butyldimethylchlorosilane (364 g, 2.41 mol) is added in portions, maintaining the internal temperature below 10° C. The reaction mixture is allowed to warm to room temperature, and stirred for 15 hours. Water (2.2 L) is added over 30 minutes. The mixture is extracted with heptane (2.2 L+0.6 L). The combined organic phases are washed with water (2×1 L), dried over anhydrous magnesium sulfate, filtered and concentrated under reduced pressure, to provide the crude (R)-silyl ether (988 g).

EXAMPLE 7

Removal of residual butyrate ester from (R)-4-[3-(trifluoromethyl)-phenoxy]-3-(tert-butyldimethylsilyloxy)-1-butyne The crude (R)-silyl ether (988 g, about 75% pure, 2.15 mmol) is dissolved in methanol (1.5 L) and potassium carbonate (37 g, 0.27 mol) is added. The mixture is stirred for 3 hours, after which the methanol is removed under reduced pressure. Water (1.5 L) and heptane (1.5 L) are added to the residue, the mixture is stirred, and the layers are separated. The organic layer is washed and water (0.7 L), dried over anhydrous magnesium sulfate, filtered and evaporated to dryness. The residue is dissolved in dichloromethane (1.5 L) and phthalic anhydride (78 g, 0.53 mol) and triethylamine (87 ml, 0.63 mol) are added. The solution is stirred for 2 hours, after which the solvent is removed under reduced pressure and 10% sodium carbonate solution (0.7 L) heptane (2.2 L), water (4.5 L) and sodium chloride (500 g) are added. After stirring vigorously, the mixture is allowed to partition. The heptane layer is separated, the aqueous layer is extracted with heptane (0.5 L), and the combined organic layers are washed with water (1.5 L). The heptane solution dried over anhydrous magnesium sulfate, and is passed through a silica plug (321 g). The compound is eluted with heptane (1.5 L), and after evaporation of the solvent, the (R)-silyl ether is obtained as a light yellow mobile liquid (740 g, 58% overall from the racemic propargylic alcohol); $[\alpha]_D^{23}=-28.16$ (c0.98, $CH_2Cl_2$). $^1H$ nmr: 200 MHz ($CDCl_3$) δ ppm 0.12 (3 H, s), 0.16 (3 H, s), 0.93 (9 H, s), 2.49 (1 H, d, J2 Hz), 4.10 (2 H, d, J6 Hz), 4.75 (1 H, td, J6.2 Hz), 7.05–7.16 (2 H, m), 7.24 (1 H, d, J8 Hz), 7.40 (1 H, t, J 8 Hz). After removal of the TBDMS group from a small sample with HCl/MeOH, chiral HPLC analysis of the propargylic alcohol showed the enantiomeric excess to be >99%.

EXAMPLE 8

(R)-4-[3-(Trifluoromethyl)phenoxy]-1-butyn-3-yl butyrate by bioresolution and removal of (S)-alcohol as the hemisulfate ester 4-[3-(Trifluoromethyl)phenoxy]-1-butyn-3-ol (14.51 kg, 63.0 mol), heptane (49.6 kg) and vinyl butyrate (9.96 kg, 94.6 mol) are charged to a nitrogen-purged vessel. The starting alcohol is washed through with heptane (3.4 kg). The temperature of the vessel contents are adjusted to 21–23° C. and Mucor miehei lipase (2.94 kg) is charged. The mixture is stirred unit 50% conversion to the (R)-butyrate is reached (approximately 48 h) and the enzyme is removed by filtration. The vessel is charged with heptane (16.5 kg) to the vessel and discharged via the filter to wash the enzyme. The vessel is cleaned out using water and then methanol, dried out and all the lines blown clear. The combined organic phases are charged to the vessel followed with a 3.4 kg heptane wash. Vacuum and hearing are applied to distill heptane (target 68 kg), maintaining the temperature below 50° C. The vessel contents are cooled back to 18–22° C. Dimethylformamide (16.5 kg) is charged and sulphur trioxide-pyridine complex (6.0 kg, 37.7 mol) is added in portions. The internal temperature of the reaction is maintained below 25° C. Heptane (18.2 kg) is charged, then 25% sodium carbonate solution is charged in portions checking the pH of the solution. Addition is continued with addition until the pH is in the range 7.0–7.5 (approx. 15 kg of carbonate solution). Water (~52.5 kg) is charged so that the combined mass of sodium carbonate solution and water charged is 69.9 kg. The mixture is stirred until the solids have dissolved (~1 hr). After settling, the lower aqueous phase is removed to drum and the heptane solution is concentrated by distillation of heptane (8.4 kg) under reduced pressure (max temp. 50° C.) to give the title compound as a heptane solution (10.4 kg containing 8.5 kg title compound, 49% yield, ~93% ee) which is used directly in the next step.

EXAMPLE 9

(R)-4-[3-(Trifluoromethyl)phenoxy]-1-butyn-3-ol where the butyrate has an enantiomeric excess of <90%

Potassium dihydrogen phosphate (310 g, 2.28 mol) and water (44.0 kg) are charged to a nitrogen-purged vessel. The mixture is stirred until the phosphate salt has dissolved, and the temperature is adjusted to 28–32° C. 10% Potassium hydroxide solution (~0.56 kg) is titrated is until pH 6.9–7.1 is reached. The butyrate ester (8.5 kg, 28.3 mol)/heptane solution is charged and washed through with heptane (4 kg). Candida antartica lipase (190 g) is added and the mixture is stirred at 30° C. while titrating to pH 7 using 4 N sodium hydroxide solution (~6.2 kg). After 12 hours, toluene (13.1 kg) is charged. The enzyme is filtered off, washing through with toluene (3 kg). The vessel is cleaned out using water and then methanol, and dried out. The lines are blown clear. The mixture is charged back to the vessel, followed by a toluene wash (3 kg). The aqueous layer is removed and a vacuum (~130 torr) is applied. The organic layer is dried by azeotropic removal of water with a maximum temperature of 50–60° C. The solution is transferred to a rotary evaporator and the solvent is removed under reduced pressure to give the (R)-alcohol as an orange oil (6.3 kg, ~90% w/w, ~86% yield, <98% ee), containing unwanted butyrate ester (~4.8%).

EXAMPLE 10
(R)-4-[3-(Trifluoromethyl)phenoxy]-3-tert-butyldimethylsilyloxy-1-butyne, omitting steps vii and viii The crude (R)-alcohol (~90% w/w, 6.3 kg, 5.7 kg, AI, 24.8 mol), imidazole (2.4 kg, 35.3 mol) and DMF (10.8 kg) are charged to a vessel. t-Butyldimethylchlorosilane (4.03 kg, 26.7 mol) is charged in portions, maintaining the internal temperature below 10° C. during the addition. The mixture is cooled to 4° C., stirred for 2 hrs and the vessel contents is adjusted to 18–25° C. Water (25.0 kg) and heptane (17.1 kg) are charged, the mixture is stirred, allowed to settle and the phases are separated. The organic phase is charged to a rotary evaporator and the solvent is distilled under reduced pressure (Max bath temp. 60° C.) to provide the crude silyl ether as a pale yellow mobile liquid (9.1 kg, assumed to be ~93% w/w and 8.4 kg AI). The crude silyl ether is purified in 7×1.3 kg portions by applying to a silica plug (1.06 kg, 1.5:1 width to height ratio. 16.5 cm by 11.0 cm.) and elution with heptane (3×3.4 kg) under a slight vacuum. The combined organic phases are charged to a rotary evaporator, transferring with the aid of heptane washes (2×0.7 kg), and the heptane is distilled under reduced pressure (10–20 torr, max temp. 50–55° C.), to give the (R)-silyl ether as colourless oil (1.09 kg per batch, 7.5 kg of product in total).

EXAMPLE 11
(R)-4-[3-(Trifluoromethyl)phenoxy]-3-(tert-butyldimethylsilyloxy)-1-iodo-1E-butene A dry 5 L 3-necked flask is purged with nitrogen, and bis(cyclopentadienyl)-zirconium dichloride (459 g, 1.57 mol) and toluene (2 L) are added. The vessel is covered with aluminum foil to exclude light, evacauted and purged with nitrogen. tert-Butylmagnesium chloride (2 M in ether, 785 ml) is added over 30 minutes. The mixture is heated at 50° C. for 1 hour. During this time gas evolution is observed (isobutylene). The alkyne (450 g, 1.31 mol) in toluene (500 ml) is added, and heating is continued between 50–60° C. for 5 hours. The reaction mixture is cooled to −40° C. and a solution of iodine (497 g, 1.96 mol) in THF (600 ml) is added over 35 minutes. The mixture is warmed to room temperature over one hour, and 1 M sodium metabisulifite (2 L) is added. Heptane (3 L) is added, and a dense bright yellow precipitate is formed. The mixture is filtered through a No 3 filter paper, and the filter cake is washed with heptane (1 L). The organic layer is separated, the aqueous phase is extracted with heptane (1 L), and the combined organic phases are washed with sodium metabisulfite solution (1 M, 3 L), saturated sodium bicarbonate solution (2 L) and brine (2 L). The organic phase is dried (MgSO$_4$), filtered and concentrated under reduced pressure. The residue is passed through a pad of activated aluminium oxide (Neutral Brockmann, 1, 150 mesh, 750 g), eluting with heptane (6 L). The solvent is concentrated under reduced pressure, the residue is dissolved in heptane (1 L) and filtered through Celite. The solvent is concentrated to provide the iodide as a red/brown oil (441 g, 71.5% Th); [α]$_D^{23}$=−15.5 (c 0.96, CH$_2$Cl$_2$); $^1$H nmr: 200 MHz (CDCl$_3$) δ ppm 0.11 (6 H, s, 2), 0.92 (9 H, s), 3.91 (2 H, d, J6 Hz), 4.51 (1 H, m, CH), 6.50 (1 H, dd, J14 and 1 Hz), 6.68 (1 H, dd, J14 and 5 Hz), 7.04–7.11 (2 H, m), 7.24 (1 H, m), 7.40 (1 H, t, J 8 Hz). GC analysis shows 5–10% of 4-(3-trifluoromethylphenoxy)-3-(tert-butyldimethylsilyloxy)-1-butene to be present.

EXAMPLE 12
Bioresolution of 1-(3-chlorophenoxy)-3-butyn-2-ol

1-Chlorophenoxy-3-butyn-2-ol (19.1 g, 97 mmol) was placed in a jacketed flask, and MTBE (17 ml) and heptane (95 ml) were added. The mixture was equilibrated to 22° C., and vinyl propionate (13.2 ml, 121 mmol) and Chirazyme-L9 (4.46 g) were added. The mixture was stirred at 22° C. for 46.5 h, when chiral GC analysis showed the starting alcohol to by 87% ee (S) and the propionate to be 92% ee (R), a conversion of 48.6%. The solution was filtered and the solvent was evaporated to give the alcohol/propionate mixture as a pale yellow oil.

EXAMPLE 13
Mesylation

The alcohol/propionate mixture was dissolved in MTBE (100 ml), and the solution was cooled to 5° C. Triethylamine (10.8 ml, 78 mmol) was added. The solution was cooled to 0–2° C. and methanesulfonyl chloride (3.75 ml, 48.5 mmol) was added over 30 minutes, maintaining the internal temperature at 0–2° C. The suspension was stirred at 0–2° C. for 15 minutes, and extra methanesulfonyl chloride (0.2 ml, 2.6 mmol) was then added. The suspension was stirred at 0–2° C. for 5 minutes, and then the reaction was quenched with water (85 ml). The aqueous layer was removed, and the organic layer was washed with saturated potassium hydrogen sulfate solution-water (1:1, 80 ml), saturated sodium bicarbonate solution (80 ml) and brine (40 ml). After drying (MgSO$_4$), filtration and evaporation of the solvent, the mesylate/propionate mixture was obtained as a yellow oil (26 g). $^1$H nmr (200 MHz, CDCl$_3$) δ ppm 7.27–6.92 (2 H total, m), 6.84–6.78 (1 H total, m) 5.74 (1 H propionate, td, J5.8, 2.3 Hz), 5.51 (1 H mesylate, td, J5.6, 2.4 Hz), 4.25 (2 H, mesylate, d, J 4.9, 4.19 (1 H propionate, d, J5.5 Hz), 3.16 (3 H mesylate, s), 2.79 (1 H mesylate, J2.4 Hz), 2.53 (1 H propionate, J2.1 Hz), 2.39 (2 H propionate, q, J7.6 Hz) and 1.16 (3 H propionate, t, J7.5 Hz)

EXAMPLE 14
(R)-1-(3-Chlorophenoxy)-3-butyn-2-yl propionate

Triethylamine (12 ml) was added to propionic acid (7.2 ml, 97 mmol) over 15 minutes. The mesylate/propionate mixture (26 g) was added, washing in with triethylamine (1.5 ml, total 13.5 ml, 97 mmol). The reaction flask was purged with nitrogen, and the mixture was heated to 110–120° C. for 4 h, then allowed to cool to room temperature. The mixture was diluted with heptane (80 ml) and saturated sodium bicarbonate solution (80 ml) was added cautiously while stirring. The layers were separated and the aqueous layer was extracted with heptane (20 ml). The combined organic layers were washed with saturated potassium hydrogen sulfate solution-water (1:1, 80 ml), saturated potassium hydrogen sulfate solution (80 ml), saturated sodium bicarbonate solution (80 ml), (MgSO$_4$) and filtered. After evaporation of the solvent, the crude propionate was obtained as a brown oil (20.3 g).

EXAMPLE 15
Removal of residual alcohol from crude (R)-propionate

The crude propionate (20.3 g, 80.3) was dissolved in anhydrous DMF (20 ml). Sulfur trioxide-pyridine complex (1.28 g, 8.03 mmol) was added. The solution was stirred at room temperature for 1 h. The solution was diluted with heptane (80 ml) and saturated sodium bicarbonate solution (40 ml) was added cautiously while stirring. Water (40 ml) was added and the layers were separated. The organic layer was washed with saturated potassium hydrogen sulfate solution-water (1:1, 80 ml),), dried (MgSO4) and filtered. After evaporation of the solvent, the alcohol-free propionate was obtained as a brown oil (19.3 g, 79% from the racemic alcohol). $^1$H nmr (400 MHz, CDCl$_3$) δ ppm 7.21 (1 H, t, J8.1 Hz), 6.98 (1 H, dr, J7.9, 1.0 Hz), 6.95 (1 H, t, J2.2 Hz), 6.83 (1 H, ddd, J8.4, 2.5, 1.0 Hz), 4.76–5.73 (1 H, m), 4.23–4.10 (2 H, m), 2.53 (1 H, d, J2.4 Hz), 2.47–2.32 (2 H, m) and 1.16 (3 H, t, J7.6 Hz). ee 79% by chiral GC.

EXAMPLE 16
(R)-1-(3-Chlorophenoxy)-3-butyn-2-ol

Approximately 50 mM phosphate buffer was prepared in a jacketed flask by dissolving potassium dihydrogen orthophosphate (1.04 g, 7.63 mmol) in water (150 ml). The solution was equilibrated to 30° C. then titrated to pH 7 with approximately 2 M potassium hydroxide solution. A solution of sodium hydroxide (3.24 g, 81 mmol) in water (20 ml) was also prepared. A solution of the (R)-propionate (24.1 g, 95 mmol) in heptane 22 ml was added to the buffer solution. Chirazyme-L2 (440 mg) was added, and the mixture was stirred vigorously at 30° C. for 4 h while titrating to pH 7 with the sodium hydroxide solution. 19 ml (approximately 77 mmol) of sodium hydroxide solution was used. The mixture was diluted with toluene (50 ml), filtered (Celite), washing through with toluene (30 ml) and the layers were separated. The organic layer was washed with saturated sodium bicarbonate solution (2×80 ml), dried (MgSO$_4$), then filtered through a silica plug (20 g), eluting with heptane-MTBE (2:1, 200 ml). After evaporation of the solvent, toluene (50 ml) and heptane (150 ml) were added. The solution was cooled to −10° C. over 30 minutes while stirring. Crystallisation began at 10° C. The suspension was stirred at −10° C. for 30 minutes then filtered. The crystals were washed with cold (−20° C.) heptane-toluene (3:1) then dried to give the (R)-alcohol as a fine white solid (10.9 g, 58.1%). mp onset 48° C. by DSC. $[\alpha]_D^{25}$−24.4°, $[\alpha]_{578}^{25}$−25.4°, $[\alpha]_{546}^{25}$−28.9°, $[\alpha]_{436}^{25}$−49.6°, $[\alpha]_{405}^{25}$−60° and $[\alpha]_{365}^{25}$−80.3° (c=1.0, CHCl$_3$), $^1$H nmr (400 MHz, CDCl$_3$) δ ppm 7.20 (1 H, t, J8.1 Hz), 6.96 (1 H, dr, J7.9, 1.0 Hz), 6.93 (1 H, t, J2.2 Hz), 6.81 (1 H, ddd, J8.4, 2.5, 1.0 Hz), 4.77–4.73 (1 H, m), 4.11 (1 H, dd, J9.4, 3.9 Hz), 4.06 (1 H, dd, J9.9, 6.9 Hz), 2.65 (1 H, d, J5.4 Hz) and 2.53 (1 H, d, J2.5 Hz). Found: C 61.09%, H 4.64% and Cl 17.91%, C$_{10}$H$_9$ClO$_2$ requires C 61.08%, H 4.61% and Cl 11.40%. ee after derivation with trifluoroacetic anhydride >99% by chiral GC.

EXAMPLE 17
(R)-4-(3-Chlorophenoxy)-3-tert-butyldimethylsilyloxy-1-butyne

The (R)-alcohol (10.8 g, 55 mmol) was dissolved in DMF (11 ml). Imidazole (7.86 g, 115 mmol) was added. When the solution was homogeneous, it was cooled in an ice-water bath and tert-butyldimethylsilyl chloride (8.70 g, 57.7 mmol) was added over 15 minutes. The solution was stirred allowed to warm to room temperature and stirred at room temperature for 2 h. The reaction was quenched cautiously by adding water (75 ml) over 15 minutes, then heptane (75 ml) was added. The organic layer was separated and washed with water (2×75 ml), dried (MgSO$_4$), then filtered through a silica pad (5 g), eluting with heptane (75 ml) to give the silyl ether as a colourless, mobile oil (17.0 g, 99.5%). $[\alpha]_D^{25}$ −30.7°, $[\alpha]_{578}^{25}$ −32.0°, $[\alpha]_{546}^{25}$ −36.4°, $[\alpha]_{436}^{25}$ −61.5°, $[\alpha]_{405}^{25}$ −73.9° and $[\alpha]_{365}^{25}$ −96.1° (c=1.2, CHCl$_3$), $^1$H nmr (400 MHz, CDCl$_3$) δ ppm 7.19 (1 H, t, J8.1 Hz), 6.95–6.91 (2 H, m), 6.80 (1 H, ddd, J8.4, 2.5, 1.0 Hz), 4.72 (1 H, td, J5.9, 2.5 Hz), 4.08–4.01 (2 H, m), 2.47 (1 H, d, J2.0 Hz), 0.91 (9 H, s), 0.16 (3 H, s) and 0.13 (3 H, s). found: C 61.78%, H 7.39% and Cl 11.45%, C$_{16}$H$_{23}$ClO$_2$Si requires C 61.81%, H 7.46% and Cl 11.40%. ee after removal of TBDMS with HCl/MeOH and derivatisation with trifluoroacetic anhydride >99% by chiral GC.

EXAMPLE 18
(E)-1-Iodo-4-(3-chlorophenoxy)-3(R)-tert-butyldimethylsilyloxy-1-butene Zirconocene dichloride (9.35 g, 32.0 mmol) and toluene (50 ml) were added to a 250 ml 3-necked flask which was then flushed with nitrogen and maintained under a nitrogen atmosphere. The flask was covered with foil to exclude light. The mechanical stirrer was started and tert-butylmagnesium chloride (2 M, 16.0 ml, 32.0 mmol) added. The mixture was heated to 50° C. for 1 h. The alkyne (8.29 g, 26.66 mmol) in toluene (20 ml) was added and heating continued for a further 5 h. The hearing mantle was removed and the reaction allowed to cool to room temperature. The flask was then cooled in a CO$_2$/acetone bath to −40° C. A solution of iodine (10.15 g, 40.0 mmol) in tetrahydrofuran (20 ml) was added over 10 minutes (keeping the temperature below −33° C.). The cold bath was removed and the reaction allowed to warm to room temperature (a water bath at 20° C. was used). After 20 minutes, the reaction wa re-cooled to 10° C. and aqueous sodium metabisulfite (1 M, 100 ml) was added (temperature rose to 18° C.). The mixture was poured onto heptane (100 ml) and aqueous sodium metabisulfite (1 M, 100 ml) and then filtered to remove a dense yellow precipitate. The filter cake was washed with heptane (100 ml). The organic phase was separated and the aqueous layer was extracted with heptane (100 ml). The combined organic phases were washed with aqueous sodium metabisulfite (1 M, 100 ml), saturated aqueous sodium hydrogencarbonate (100 ml) and brine (100 ml), dried (MgSO$_4$), filtered and evaporated. The crude product was purified by filtration through a pad of neutral alumina (40 g), eluting with heptane (300 ml) and then 5% MTBE in heptane. The solvent was evaporated to give a slightly cloudy yellow/organe oil. The purification step was repeated using a pad of alumina (10 g) over a bed of Celite and eluting with heptane (250 ml). Evaporation of solvent afforded the vinyl iodide as a clear yellow/orange oil (8.77 g, 20.2 mmol, 75%) containing approx. 10% alkene. $[\alpha]_D^{20}$ −31.8° (c=1.0, CH$_2$Cl$_2$). $^1$H nmr (200 MHz, CDCl$_3$) δ ppm 7.20 (1 H, t, J8), 6.97–6.88 (2 H, m), 6.80–6.74 (1 H, m), 6.67 (1 H, dd, J14.5, 5), 6.48 (1 H, dd, J 14, 7), 4.51–4.43 (1 H, m), 3.85 (2 H, d, J6), 0.91 (9 H, s) and 0.10 (6 H, s), m/z (GCMS, EI) 381 (M-Bu, 9%), 185 (100).

Scheme I

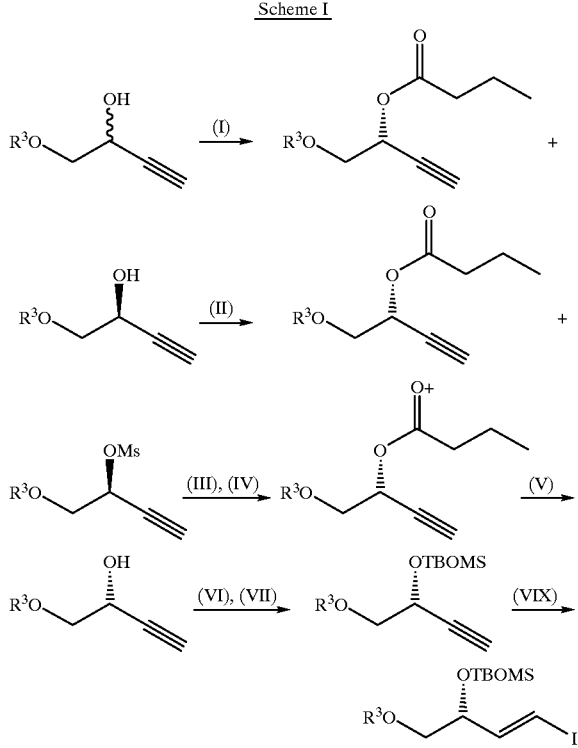

What is claimed is:

1. A process for the preparation of a propargylic alcohol, enriched in the (R)-enantiomer, of the formula

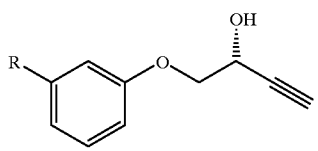

wherein R is $C_{1-4}$ alkoxy, halogen, or $C_{1-4}$ alkyl optionally substituted by OH or halogen, which comprises the steps of (a) enantioselective (R)-esterification of the racemic alcohol using any acyl donor and a first enzyme;

(b) removal of the untreated (S)-alcohol; and (c) enantioselective hydrolysis of the (R)-ester, using a second enzyme.

2. The process according to claim 1, wherein the product is in at least 97% enantiomeric excess.

3. The process according to claim 2, wherein the product is in at least 99% enantionmeric excess.

4. The process according to claim 1, wherein the first enzyme is Mucor miehei lipase.

5. The process according to claim 1, wherein the removal comprises conversion of the unreacted (S)-alcohol to a derivative more readily separable from the (R)-ester, and separation of the derivative.

6. The process according to claim 5, wherein the derivative is the hemisulfate ester.

7. The process according to claim 1, wherein the removal comprise conversion of the unreacted (S)-alcohol to the (R)-ester, by conversion of the OH group to a leaving group displaceable by the acyloxy group, and displacement with inversion using an acyloxy donor.

8. The process according to claim 7, wherein the leaving group is an alkenesulfonate or arenesulfonate group, and the displacement comprises using a carboxylic acid or a salt thereof.

9. The process according to claim 8, wherein the leaving group is methanesulfonate or p-toluenesulfonate.

10. The process according to claim 1, wherein the ester is the butyrate or propionate.

11. The process according to claim 1, wherein the second enzyme in Candida antarcitica lipase.

12. The process according to claim 1, wherein R is $CF_3$.

13. The process according to claim 1, wherein R is Cl.

* * * * *

UNITED STATES PATENT AND TRADEMARK OFFICE
CERTIFICATE OF CORRECTION

PATENT NO.    : 6,214,611 B1
DATED         : April 10, 2001
INVENTOR(S)   : Martin Edward Fox, Julian Simon Parratt It is certified that error appears in the above-identified patent and that said Letters Patent is hereby corrected as shown below:

Column 14,
Line 13, "enantionmeric" should read -- enantiomeric --.

Signed and Sealed this

Twenty-sixth Day of March, 2002

Attest:

Attesting Officer

JAMES E. ROGAN
Director of the United States Patent and Trademark Office